(12) United States Patent
Ganey et al.

(10) Patent No.: US 10,829,740 B2
(45) Date of Patent: *Nov. 10, 2020

(54) BIOLOGIC COMPOSITION AND METHOD OF MANUFACTURE

(71) Applicant: Vivex Biologics Group, Inc., Atlanta, GA (US)

(72) Inventors: Timothy Ganey, Tampa, FL (US); Wendy W. Weston, Miami, FL (US); Miguel Quevedo, Miami, FL (US); Stuart Oglesby, Miami, FL (US); Gaetan Jean-Robert Delcroix, Miami, FL (US); Paul C. Schiller, Miami Beach, FL (US); Gianluca D'Ippolito, North Miami Beach, FL (US)

(73) Assignee: Vivex Biologics Group, Inc., Atlanta, GA (US)

(*) Notice: Subject to any disclaimer, the term of this patent is extended or adjusted under 35 U.S.C. 154(b) by 60 days.

This patent is subject to a terminal disclaimer.

(21) Appl. No.: 16/049,215

(22) Filed: Jul. 30, 2018

(65) Prior Publication Data

US 2018/0334655 A1 Nov. 22, 2018

Related U.S. Application Data

(60) Continuation of application No. 15/591,513, filed on May 10, 2017, now Pat. No. 10,513,690, which is a division of application No. 14/683,221, filed on Apr. 10, 2015, now Pat. No. 9,675,643.

(60) Provisional application No. 62/129,337, filed on Mar. 6, 2015, provisional application No. 62/129,351, filed on Mar. 6, 2015.

(51) Int. Cl.

| | |
|---|---|
| C12N 5/077 | (2010.01) |
| A61K 35/28 | (2015.01) |
| A61K 35/32 | (2015.01) |
| A61L 27/36 | (2006.01) |
| A61L 27/38 | (2006.01) |
| A61L 27/44 | (2006.01) |
| A61L 27/58 | (2006.01) |
| A61L 27/50 | (2006.01) |
| A01N 1/02 | (2006.01) |
| A61L 27/54 | (2006.01) |
| A61K 35/12 | (2015.01) |

(52) U.S. Cl.
CPC ......... *C12N 5/0669* (2013.01); *A01N 1/0221* (2013.01); *A01N 1/0284* (2013.01); *A61K 35/28* (2013.01); *A61K 35/32* (2013.01); *A61L 27/3604* (2013.01); *A61L 27/365* (2013.01); *A61L 27/3608* (2013.01); *A61L 27/3691* (2013.01); *A61L 27/3834* (2013.01); *A61L 27/446* (2013.01); *A61L 27/50* (2013.01); *A61L 27/54* (2013.01); *A61L 27/58* (2013.01); *A61K 2035/124* (2013.01); *A61K 2300/00* (2013.01); *A61L 2430/00* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 2,622,027 A | 12/1952 | Torr | |
| 5,837,539 A | 11/1998 | Caplan et al. | |
| 9,192,695 B2 | 11/2015 | Shi | |
| 2007/0191963 A1* | 8/2007 | Winterbottom | A61F 2/28 |
| | | | 623/23.5 |
| 2010/0105132 A1 | 4/2010 | Totey et al. | |
| 2010/0124776 A1* | 5/2010 | Shi | A61L 27/3834 |
| | | | 435/177 |
| 2012/0053692 A1* | 3/2012 | Voor | A61L 27/425 |
| | | | 623/16.11 |
| 2013/0071358 A1 | 3/2013 | Peterson | |
| 2014/0065240 A1* | 3/2014 | Mitsialis | A61P 11/00 |
| | | | 424/577 |
| 2016/0030639 A1 | 2/2016 | Shi | |

FOREIGN PATENT DOCUMENTS

| | | | | |
|---|---|---|---|---|
| WO | WO 2014/159662 | * | 10/2014 | G01N 1/34 |
| WO | 2015016761 | | 2/2015 | |

OTHER PUBLICATIONS

ATCC, Thawing, Propagating and Cryopreserving Protocol for NCI-PBCF-CRL, A-375 Malignant melanoma cells, Sep. 12, 2013, retrieved from the internet Mar. 18, 2020: https://physics.cancer.gov/docs/bioresource/skin/NCI-PBCF-CRL1619_A-375_SOP-508.pdf (Year: 2013).*
Deak et al., Cytotherapy, 2010; 12: 260-264 (Year: 2010).*
Lorincz et al., Journal of Extracellular Vesicles, 2014, 3:1, 25465, pp. 1-8 (Year: 2014).*
Bone Structure and Function; ASBMR educational materials; https://depts.washington.edu/bonebio/ASBMRed/structure.html.

(Continued)

*Primary Examiner* — Scott Long
*Assistant Examiner* — Evelyn Y Pyla
(74) *Attorney, Agent, or Firm* — David L. King (57) ABSTRACT

A biological composition has a mixture of mechanically selected allogeneic biologic material derived from bone marrow. The mixture has non-whole cellular components including vesicular components and active and inactive components of biological activity, cell fragments, cellular excretions, cellular derivatives, and extracellular components. The mixture is compatible with biologic function.

5 Claims, 7 Drawing Sheets

(7 of 7 Drawing Sheet(s) Filed in Color)

(56) References Cited

OTHER PUBLICATIONS

Cells and Organelles; http://biology.cld.uc.edu/courses/bio104/cells.htm.
Derivative definition; Merriam Webster; http://www.merriam-webster.com/dictionary/derivative.
E.Linetsky, N.Kenyon, H.Li, X.Xu and C.Ricordi; Increased Immunogenicity of Human Vertebral Body Marrow After Processing in Bovine Versus Human Serum Albumin; Elsevier Science Inc.; Transplantation Proceedings 29, 1960 (1997).
Matsumura, Kazuaki; Hyon, Suong-Hyu; Polampholytes as low toxic efficient cryoprotective agents with antifreeze protein properties; Biomaterials 30, 2009, 4842-4849.
Nottestad, Sheri Y.; Baumel, Julian J.; Kimmel, Donald B.; Recker, Robert R. and Heany, Robert P; The Proportion of Trabecular Bone in Human Vertebrae; Journal of Bone and Mineral Research, vol. 2, No. 3 1987.
Oryan et al; Bone regenerative medicine: classic options, novel strategies, and future directions, Journal of Orthopaedic Surgery and Research, 2014, vol. 9:18, pp. 1-27.

* cited by examiner

Percent recovery from freeze at 6 Months

BIOLOGIC COMPOSITION AND METHOD OF MANUFACTURE

RELATED APPLICATIONS

This invention is a continuation of co-pending U.S. application Ser. No. 15/591,513 filed on May 10, 2017 which is a division of U.S. application Ser. No. 14/683,221 filed on Apr. 10, 2015 entitled, "Biologic Composition And Method Of Manufacture" now U.S. Pat. No. 9,675,643 issued on Jun. 13, 2017.

TECHNICAL FIELD

This invention is a tissue regenerative biological composition. More specifically, a composition at least in part formed from bone marrow and a method of manufacture and use of said composition.

BACKGROUND OF THE INVENTION

In the area of tissue regeneration or repair, the use of stem cell therapy has been widely touted.

Often, these inventions describe isolating the stem cells, purifying and culturally expanding mesenchymal stem cells. In U.S. Pat. No. 5,837,539, entitled "Monoclonal Antibodies For Human Mesenchymal Stem Cells", Arnold Caplan et al. reported that the cells are preferably culturally expanded, but suggest it is possible to use the stem cells without culture expansion. Caplan also describes a way to isolate stem cells.

A major technological hurdle to producing a safe allogeneic composition with viable cells has been the need to approach a fraction of risk approaching zero by removing all antigenic properties that lead to inflammation factors in a separation to yield only a certain stromal cell type. This has proven both difficult and degrading the quantity of viable cells that can be effectively harvested.

The present invention has yielded a biological composition that is safe and achieves high yields of viable stromal cells and does so in a method that allows the resultant mixture to be recovered in a non-expanded and non-differentiated way from bone marrow wherein the mixture unexpectedly exhibits increased CD105 and STR01 markers at time of use when compared to the quantity at the time of actual processing. This evidences a maintenance of viable cells in the dose, an increase in mesenchymal cells in the dose and a legacy or memory of the lineages from where the cells came which retain the ability to differentiate into new tissue forms other than bone.

These and other benefits of the present invention and the method of preparing it are described hereinafter.

SUMMARY OF THE INVENTION

A biological composition has a mixture of mechanically selected allogeneic biologic material derived from bone marrow. The mixture has non-whole cellular components including vesicular components and active and inactive components of biological activity, cell fragments, cellular excretions, cellular derivatives, and extracellular components. The mixture is compatible with biologic function.

The mixture of mechanically selected material derived from bone marrow further can have non-expanded whole cells. The biological composition preferably has bone. The bone can be added to the mixture derived from bone marrow. The bone includes a mixture of cortical bone and cancellous bone.

The combination of non-whole cell components with a select number of the non-expanded cells sustains pluripotency in the cells. The select number of the non-expanded cells includes differentiated committed cells and non-differentiated and non-committed cells.

In a preferred embodiment, the biological composition is predisposed to demonstrate or support elaboration of active volume or spatial geometry consistent in morphology with that of endogenous bone. The biological composition extends regenerative resonance that compliments or mimics tissue complexity. The mixture is treated in a protectant or cryoprotectant prior to preservation or cryopreservation. The protectant or cryoprotectant creates a physical or electrical or chemical gradient or combination thereof for tissue regeneration. The gradient can have a physical characteristic of modulus or topography. The gradient can have a chemical characteristic of spatially changing compositions of density or species of functional molecules. Also, the gradient can have an electrical characteristic of charge based or pH based or electron affinities that confer metastability in biologic potential.

The bone marrow mixture which is derived from a cadaver has separation-enhanced cell vitality including one or more of the following: separating the cells heightens their vitality, reversing "arrest" of donors, responsive molecular coupling, matrix quest in neutralizing inflammation or satience by balancing stimulus for repair. The protectant or cryoprotectant can be a polyampholyte. The regenerative resonance occurs in the presence or absence of a refractory response. When using a cryoprotectant, the cryopreservation occurs at a temperature that is sub-freezing wherein the cryopreservation temperature is from 0 degrees C. to −200 degrees C.

The biological composition's non-whole cellular component also can include organelle fragments and the active and inactive components of biological activity which can also include extants of the human metabolome.

A method of making a biological composition of the present invention has the steps of: collecting, recovering and processing bone marrow from a cadaver donor; mechanically separating the cellular or non-cellular components or a combination thereof of bone marrow from cadaverous bone; concentrating by centrifugation and filtering; separation by density gradient centrifugation; collecting cellular or non-cellular components or a combination thereof; washing the cellular or non-cellular components or a combination thereof to create the mixture; quantifying cell concentration not to exclude zero; suspending to a mixture in a cryoprotectant; freezing the mixture; and packaging a volume of bone within the mixture or separate. At the time of use, the mixture is thawed by immersion in a warm water bath for 2-3 minutes at 37 degrees C. It is diluted in saline without spinning; and then the diluted mixture, with or without the bone being intermixed, can be implanted by packing, injection, scaffolding or any other suitable means into a patient.

Definitions

DNase—deoxyribonuclease is any enzyme that catalyzes the hydrolytic cleavage of phosphodiester linkages in the DNA backbone, thus degrading DNA.

DMEM, DMEM/LG—Dulbecco's Modified Eagle Medium, low glucose. Sterile, with: Low Glucose (1 g/L), Sodium Pyruvate; without: L-glutamine, HEPES (4-(2-hydroxyethyl)-1-piperazineethanesulfonic acid)

DPBS—Dulbecco's Phosphate Buffered Saline.

CBT-MIXER—Mixing blade for Cancellous Bone Tumbler Jar.

Cold Media—Media used during the preparation of vertebral bodies for initial processing.

Cryopreserved—Tissue frozen with the addition of, or in a solution containing, a cryoprotectant agent such as glycerol or dimethylsulfoxide.

Freeze Dried/Lyophilized—Tissue dehydrated for storage by conversion of the water content of frozen tissue to a gaseous state under vacuum that extracts moisture.

Normal Saline—0.9% Sodium Chloride Solution.

Packing Media—Media used during initial processing and storage of the processed vertebral bodies prior to bone decellularization.

PBS—Phosphate Buffered Saline.

Processing Media—Media used during bone decellularization that may contain DMEM/Low Glucose no phenol red, Human Serum Albumin, Heparin, Gentamicin and DNAse.

BRIEF DESCRIPTION OF THE DRAWINGS

The patent or application file contains at least one drawing/photograph executed in color. Copies of this patent or patent application publication with color drawing(s) will be provided by the Office upon request and payment of the necessary fee. The invention will be described by way of example and with reference to the accompanying drawings in which.

DETAILED DESCRIPTION OF THE INVENTION

With reference to the present invention which is a tissue regenerative biological composition 100 made from bone marrow 200, it is believed best understood by the methods used to process and recover the biological composition, as illustrated in the FIGS. 1-6.

Figure 1:
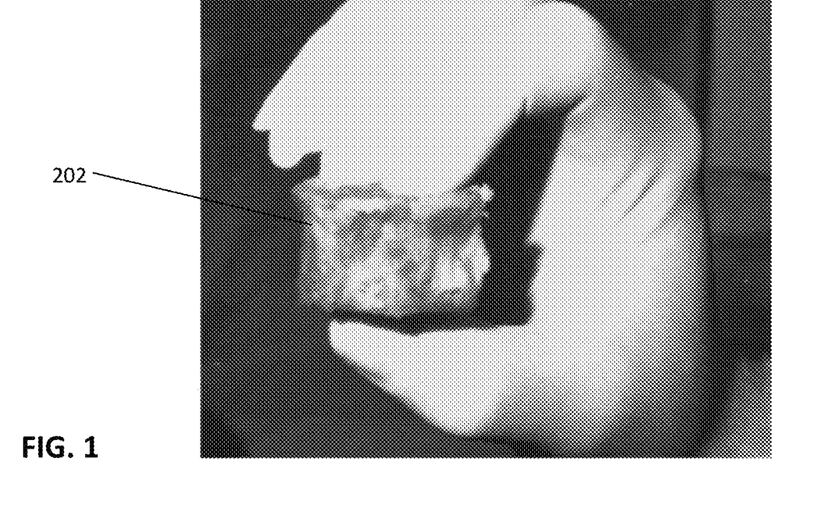
FIG. 1 shows a photograph of a cut vertebral body taken from a spine of a cadaver donor.

The first steps are to collect, recover and process bone marrow 200 from a cadaver donor. To do this, the spine is removed aseptically from the cadaver and the resultant spine segment is covered by cold media. The cold media has 0.5 ml of Heparin; 10,000 units/ml per 500 ml of DMEM. DMEM is a sterile solution with low glucose (lg/L), Sodium Pyruvate; without L-glutamine, or HEPES. This cold media is used for packaging the spine segments for later processing. At this point the spine segment includes a plurality of vertebral bodies 202. The clinical technician must remove as much soft tissue as possible and cut each vertebral body 202 with a saw. These vertebral bodies 202, once cleaned, of all adherent soft tissue around the cortical surfaces will look as shown in FIG. 1.

Figure 2:
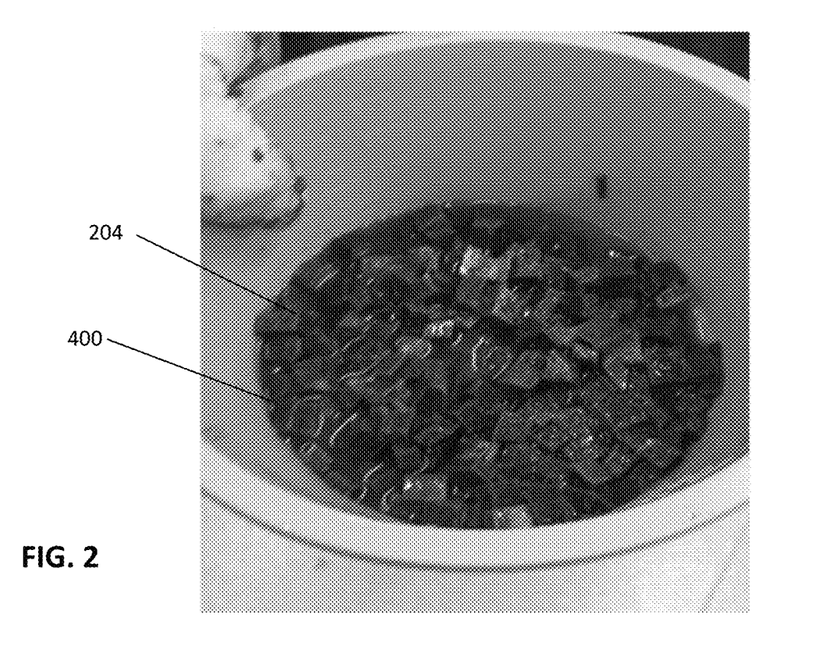
FIG. 2 shows a photograph of the vertebral body after being cut into cubic pieces and immersed in a packing media.

Once a cleaned vertebral body 202 is obtained, the next step involves cutting each vertebral body 202 into pieces, each piece 204 roughly 1 cm³. The cut pieces 204 being immersed in a packing media 400. The exemplary packing media can be DMEM with 0.5 ml Heparin and 1.25 ml of DNAse added.

Figure 3:
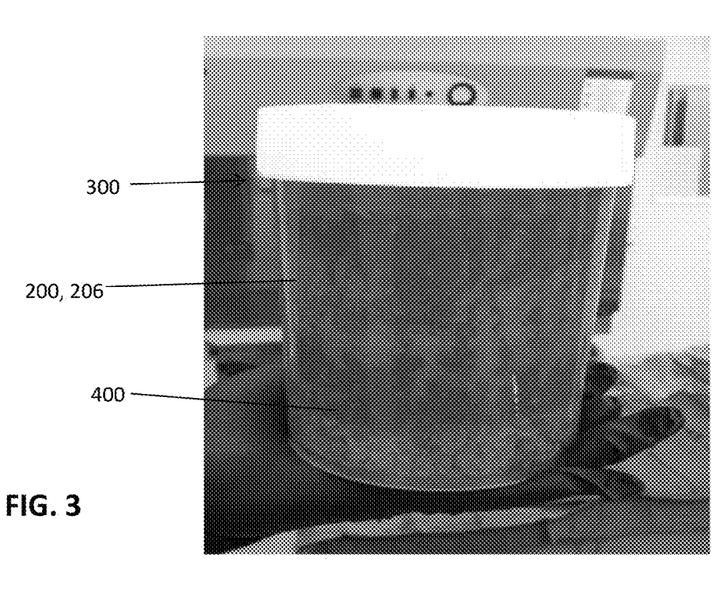
FIG. 3 shows a photograph of the bulk bone material after being ground and immersed in packing media and placed in a jar for later tumbling.

Once all the vertebral bodies 202 have been cut, the pieces 204 are taken to the bone grinder. The bone is ground into 4-10 mm pieces using packing media 400 to help the pieces go through the grinder. The ground bone 206 (bulk cortical-cancellous crushed) and all of the packing media 400, estimated volume of 500 ml are transferred into a jar 300 where 0.5-1.0 ml of Gentamicin is added to the jar 300 with ground bone 206 and packing media 400. At this point, the crushed bone 206, including cellular soft marrow 200, is intermixed.

Figure 4:
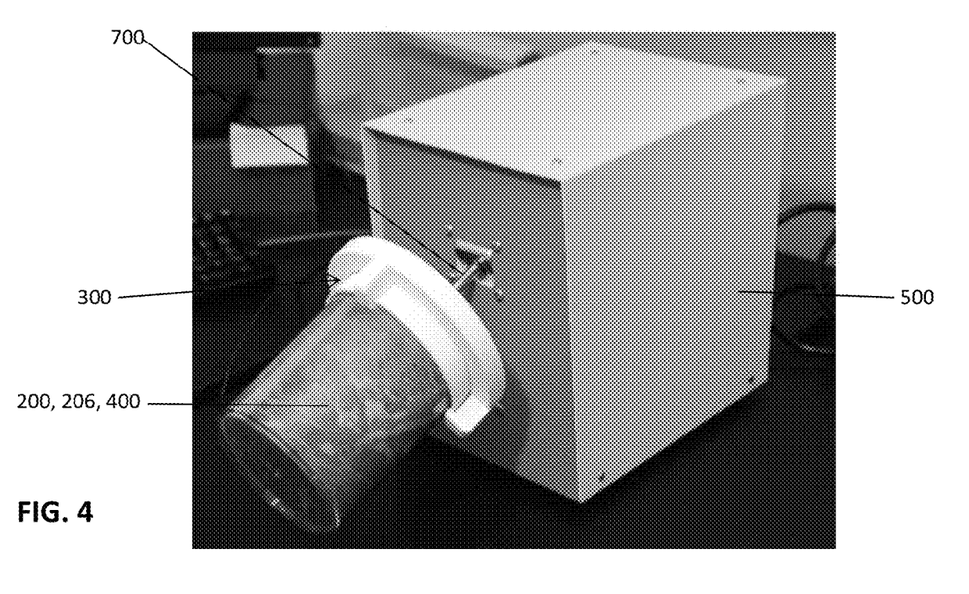
FIG. 4 shows a photograph of the jar with a CBT-Mixer connected to a tumbler.
Figure 5:
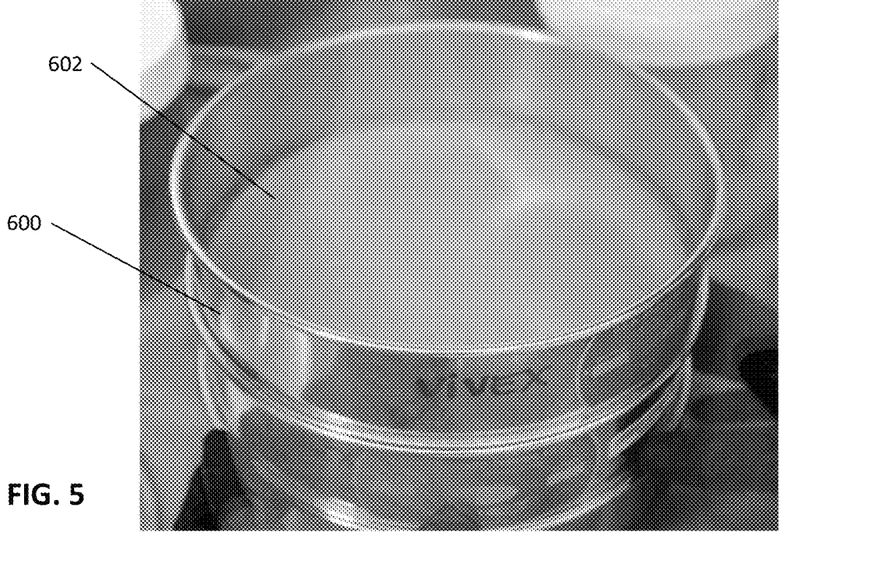
FIG. 5 is a photograph of an exemplary sieve device having sieves sized to separate the solid material.

The step of mechanically separating these cellular components of bone marrow 200 from the cadaverous bone is next performed. Transferring the bulk cortical-cancellous bone chips into a new jar with a CBT-Mixer in the jar. The bulk cortical-cancellous bone chips 206 will go through four cycles as summarized in the table below. Each cycle, after cycle 1, contains three steps using a bone tumbler 500 and sieve set 600. The sieve set 600 has screens 602 of various sizes, for example 500 μm and 180 μm, as shown in FIG. 5.

| Step | Cycle 1 | Cycle 2 | Cycle 3 | Cycle 4 |
|---|---|---|---|---|
| Bone Tumbler | 30 minutes. Using 500 mL Processing Media | 30 minutes Using 500 mL Processing Media | 30 minutes Using 500 mL Processing Media | 30 minutes Using 400 mL Processing Media |
| Sieve Set | Use the 500-μm and the bottom pan | Use the 500-μm, 180-μm and bottom pan | Use the 500-μm, 180-μm and bottom pan | Use the 500-μm, 180-μm and bottom pan |

-continued

| Step | Cycle 1 | Cycle 2 | Cycle 3 | Cycle 4 |
|---|---|---|---|---|
| | sieve. Discard decanted fluid. | sieve. Collect decanted fluid. Use decanted fluid. | sieve. Collect decanted fluid. Use decanted fluid. | sieve. Collect decanted fluid. Use decanted fluid. |
| Centrifuge | N/A | | | |

Figure 7:
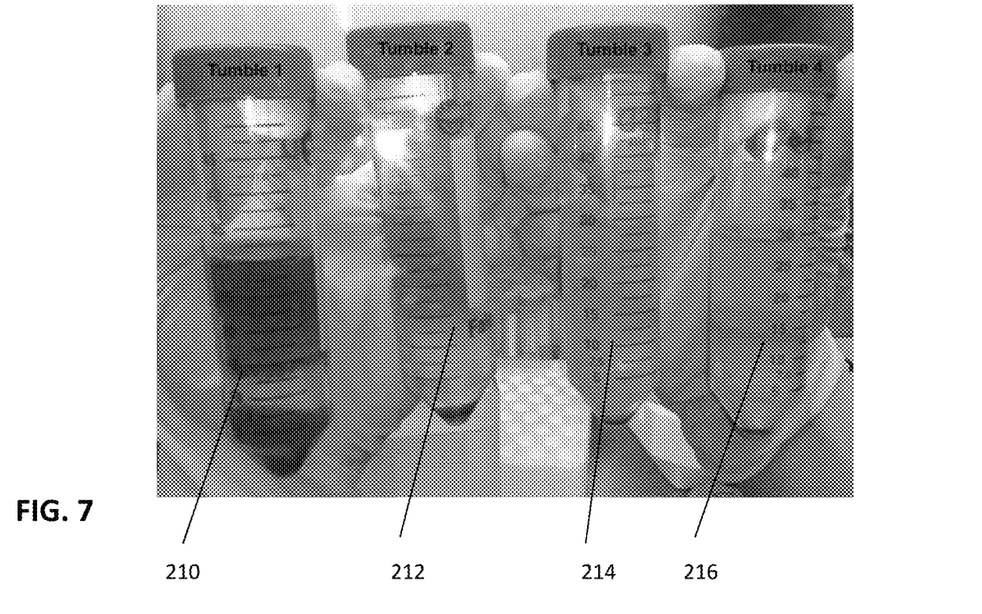
FIG. 7 is a photograph showing the four tumbling steps 1-4 by exemplary collection and Ficoll separation of the decanted fluids, the fluid in tumble 1 being completely discarded to remove unwanted debris.
Figure 8A:
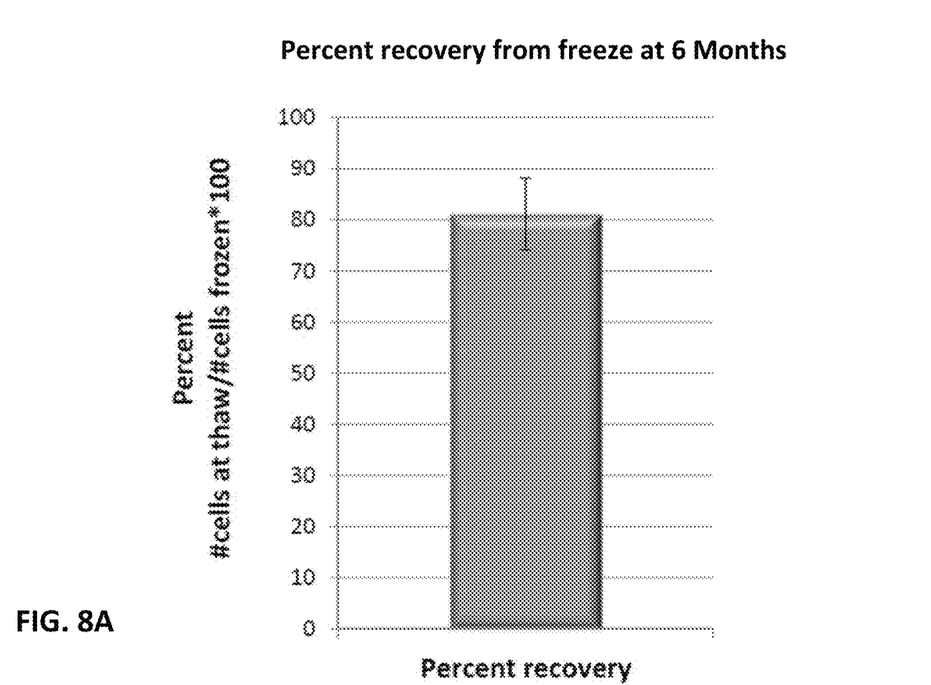
FIG. 8A is a chart showing the percent recovery at 6 months after cryofreezing the mixture of 1 ml at $1.1 \times 10^6$ cells and thawing.
Figure 8B:
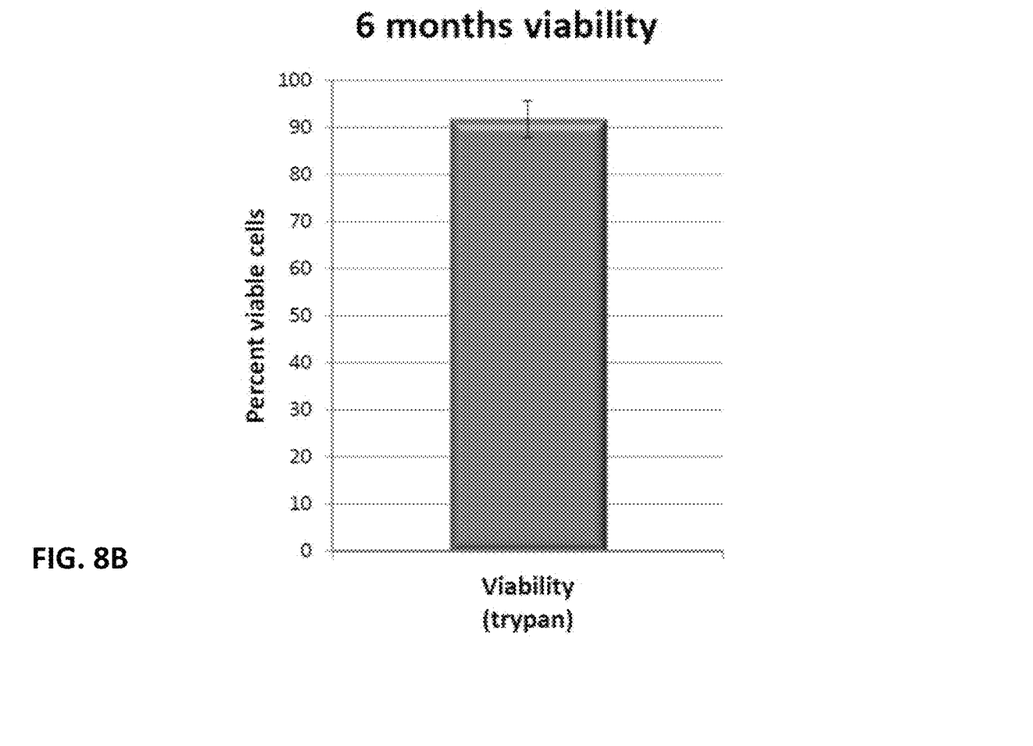
FIG. 8B is a chart showing the viability at 6 months after cryofreezing and thawing.
Figure 8C:
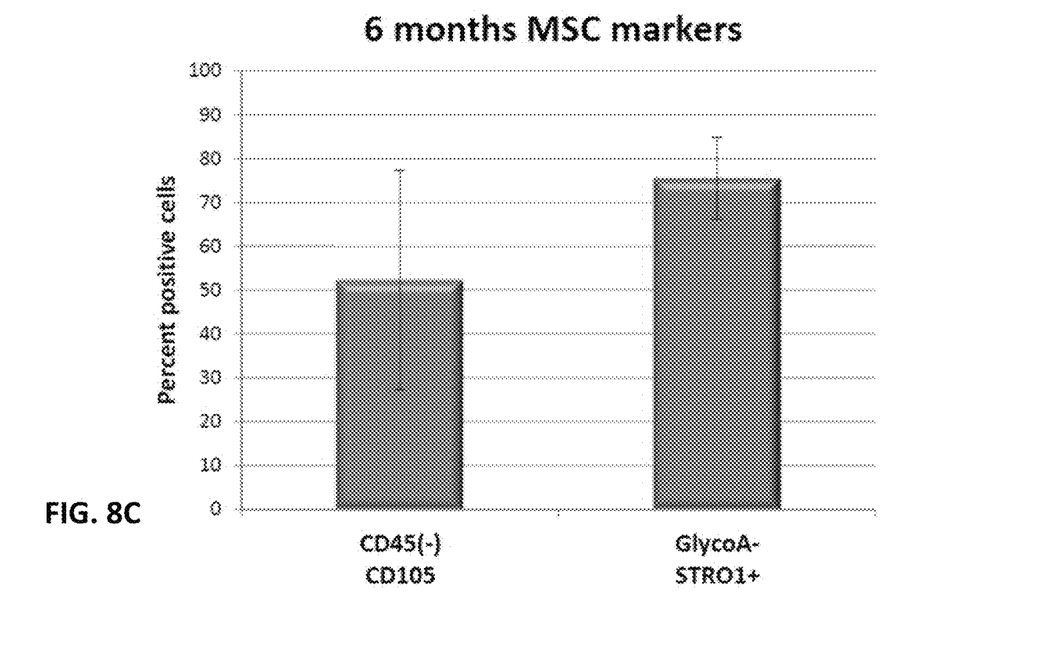
FIG. 8C shows a chart at 6 months of MSC markers by percentage of cells.

In cycle 1, the decanted fluid 210 is discarded. To best understand this, an exemplary FIG. 7 shows conical tubes with the decanted fluids after each cycle followed by Ficoll separation. Tumble 1 or Cycle 1 has most of the unwanted cells and debris as evidenced by its dark and red appearance whereas each subsequent cycle 2, 3 and 4 are progressively cleared. This FIG. 7 is only to illustrate the effects of multiple tumbles 1-4 and the value in discarding the decanted liquid 210 after the first tumble 1.

After each subsequent sieving of the bulk bone material 206, the decanted fluid 212, 214, 216 containing the mixture with whole cells is collected and put into a collection jar. When the next three cycles are complete and the decanted fluid is all placed in the collection jar comingling the fluids 212, 214 and 216 to form a decanted fluid. Then the centrifugation of the combined commingled decanted fluids 212, 214, 216 occurs by placing the fluid in a number of 250 ml conical tubes using a 100 ml pipette. The centrifuge is programmed to 280×g for 10 minutes at room temperature, preferably about 20 degrees C. The commingled decanted fluid 212, 214, 216 is passed through a blood filter to further remove any bone or spicules or clumps from the suspended cells. This completes the step of centrifuging and filtering. At this point, the mixture including whole cells 240 has been separated from the soft marrow tissue 200 and the remaining cancellous and cortical bone is discarded.

Figure 6:
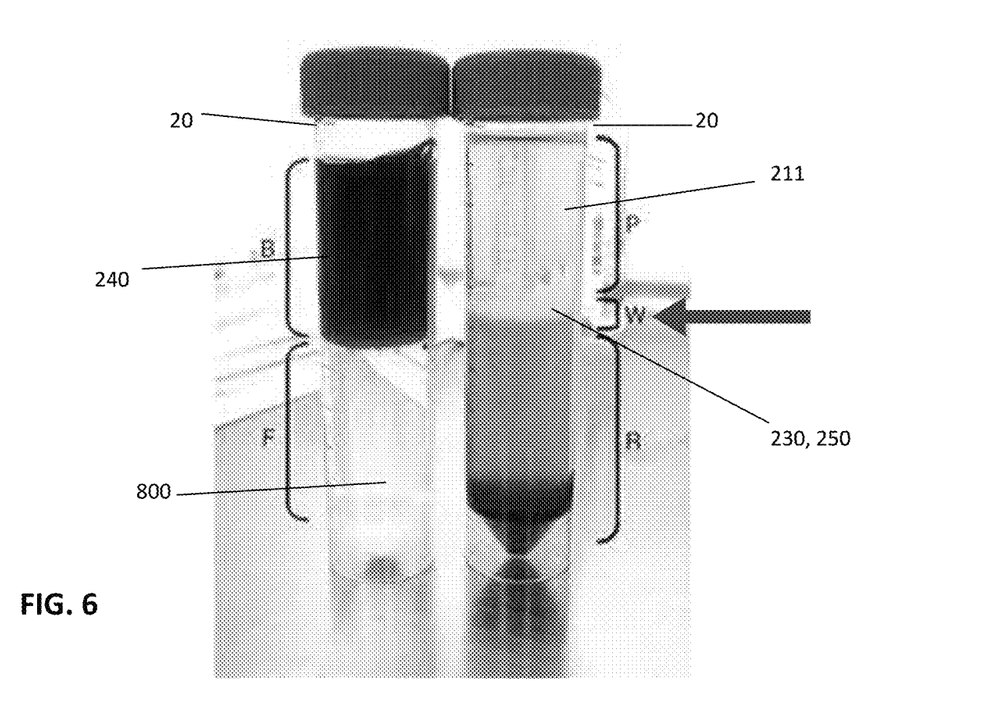
FIG. 6 shows a photograph of two 50 ml vials, the one on the left being prior to centrifuging with the Ficoll that is commercially available at the bottom and the material above it. The 50 ml vial on the right is after centrifuging showing the cell interface layer.

After this as shown in FIG. 6, the step of separating the cells 240 by a density centrifugation occurs. The mixture including whole cells 240 is placed in 50 ml conical tubes 20 with Ficoll 800 and undergoes a Ficoll-Paque separation under centrifugation wherein a cell density gradient is established by spinning at 400×g for 30 minutes at room temperature, preferably about 20 degrees C. The mixture includes cellular or non-cellular components or a combination thereof. All fluid 211 above the interface is removed and the interface 230 including the desired components which can include whole cells 250 is then collected using a 5 ml pipette and transferred into new 50 ml conical tubes ensuring no tube has more than 10 ml. Then the volume is brought to 50 ml by adding DPBS and centrifuged at 400×g for 5 minutes at room temperature, preferably about 20 degrees C. and the supernatant is removed leaving a pellet. Each 50 ml tube is then filled up to 50 ml with DPBS to resuspend the pellet. Another centrifugation occurs and the supernatant is removed and the remaining pellet is resuspended using the process media with no antibiotics. The suspension is then used to resuspend all the pellets in remaining tubes. The suspension volume is brought to 50 ml by adding processing media with no antibiotic. Then the suspension can be strained using a 100 µm cell strainer if any visual clumping is seen. These steps effectively wash the cells 250, if present, and the non-cellular components. A representative sample is then counted. The remaining, or a portion thereof, of the cellular or non-cellular components or a combination thereof is centrifuged and resuspended in the desired protectant after which it's placed in vials holding 1 ml.

In the preferred embodiment, this results in $1.1 \times 10^6$ cells per ml, but could cover any concentration from zero to less than $5.0 \times 10^6$ cells per ml depending on the desired concentration wanted per cc.

Once the cell count is established and each 1 ml suspension is established or quantified, the material is taken and suspended in a predetermined concentration of a polyampholyte cryoprotectant or any other suitable alternative protectant. When using the cryoprotectant, a freezing of the mixture at a predetermined control rate is required. Ideally, the application of a cryoprotectant coats each cell 250 and provides a protective coating to keep the cell viable during the freezing process. While the techniques for cryopreservation are well known, the present invention after being frozen has demonstrated remarkably unexpected results.

Figure 9A:
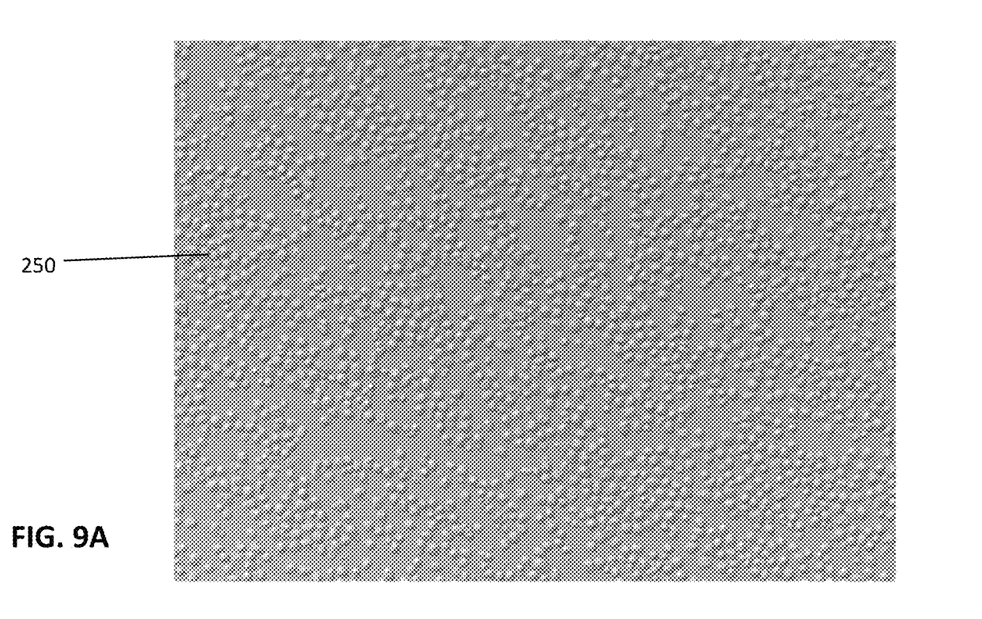
FIGS. 9A and 9B are photographs of cells thawed from a single sample and placed in media at 37 degrees C. overnight evidencing cell viability.
Figure 9B:
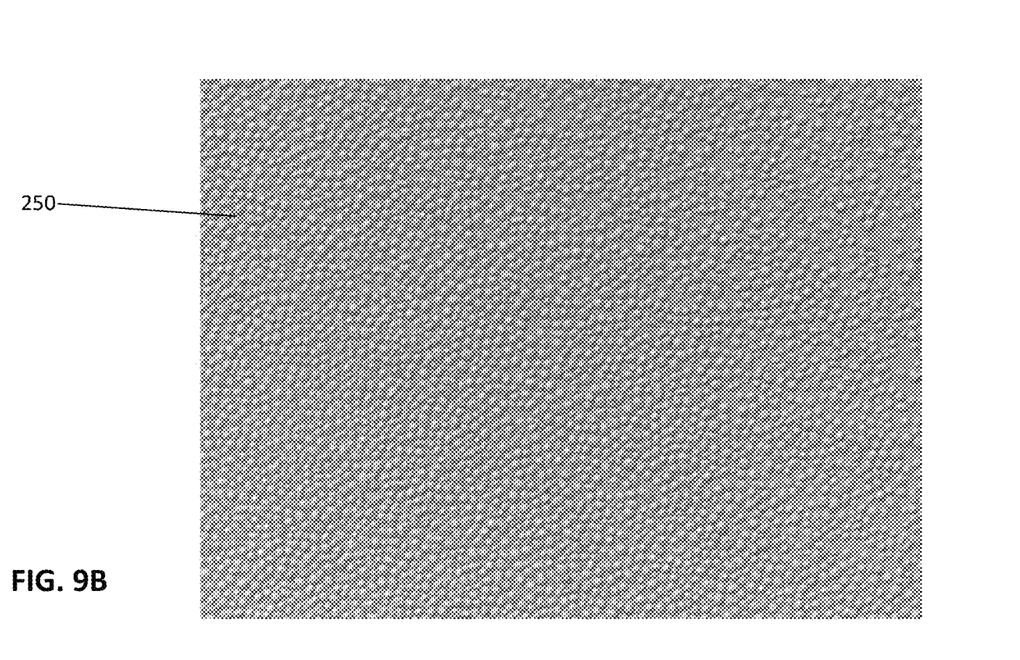

When thawed and a cell count is preformed after manufacture, the cell viability is 80 percent. Thawing is in a water bath warmed to 37 degrees C. for 2-3 minutes. After storage for 6 months, the cell viability is 91.0+/−3.8%. The percent recovery from freeze at 6 months thaw is 82.8+/−7.2%. The inventors have noted that the recovery count is lower than the viability to the lysis of undesirable GlycoA+ cells during freeze, a well-known occurrence. The unlysed desirable cells were viable at 91.0%. The inventors would also like to note that while thawed cells are generally suspended in FDS-supplemented media and spun, to better simulate how the product is actually used the cell recovery at six months was thawed and suspended in 3 ml of saline yielding a 4 ml suspension and that was not spun, but measured directly to simulate a real use injection. This allowed the cryopreservative to more effectively demonstrate that actual count of viable cells a patient would expect to receive and provides one explanation for this remarkable viability result. As shown in FIGS. 9A and 9B, the cells 250 are shown under magnification. In the cells at 6 months thaw the percent of positive cells for MSC markers, specifically CD105 and STRO1+ are 52 percent and 74 percent respectively. These indicate the majority of cells are non-differentiated and directionally favorable for new bone formation.

Figure 10:
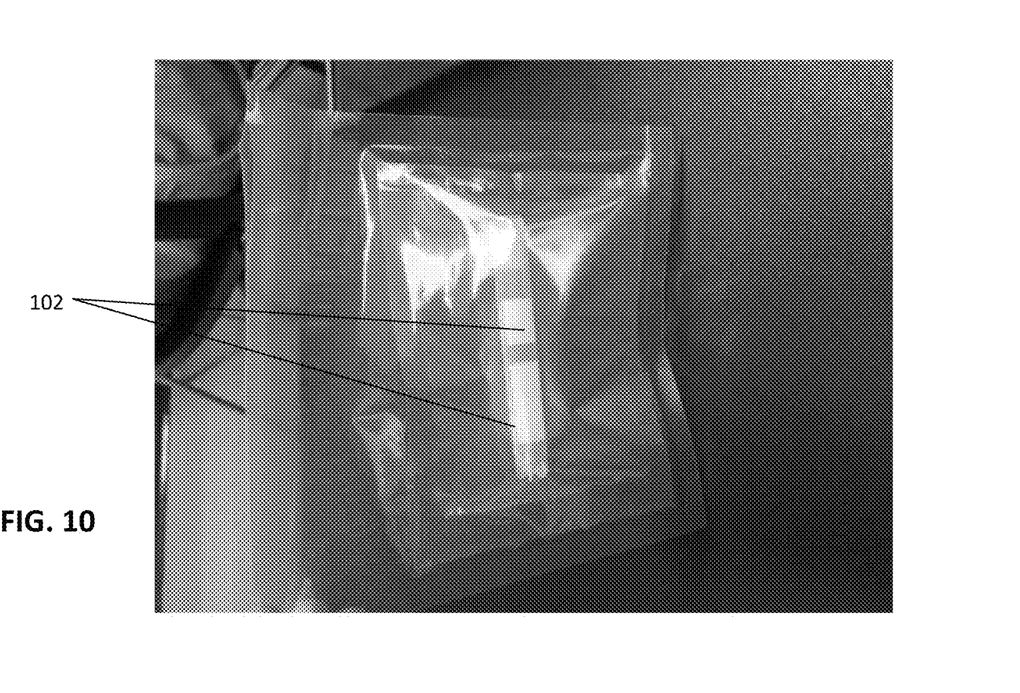
FIG. 10 is a representative photograph of the final packaging.

Once the mixture is completed, the method can include additional steps. This leads to the use of a bone blend 102 shown in FIG. 10, preferably from the same vertebral bone or at least bone from the same donor.

When the mixture is prepared, it can have whole cells or even no whole cells, but will have the mechanically selected non-whole cellular components including vesicular components and active and inactive components of biological activity, cell fragments, cellular excretions, cellular derivatives, and extracellular components.

In one embodiment, the composition includes the whole cells in the mixture. In that embodiment, it is possible to provide bone with the mixture either in the mixture or separately to be combined at the time of use.

Figure 11:
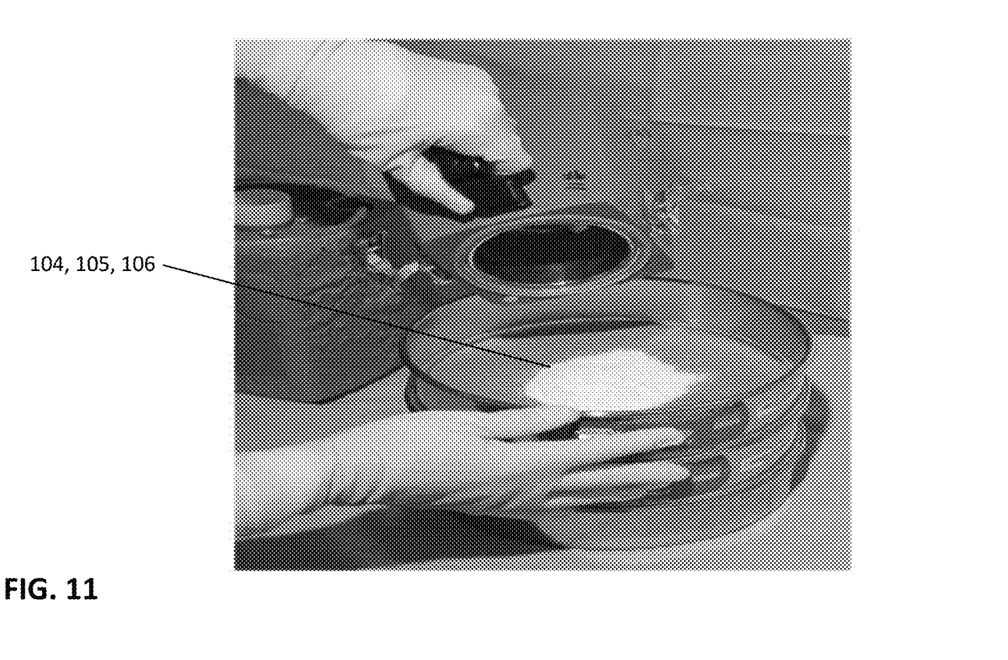
FIG. 11 is a photograph showing ground bone.

In one embodiment, the bone is ground to a size of 100 to 300 µm, see FIG. 11. Other ranges of bone sizes and mixtures can be employed depending on the application which, in this example, was bone regeneration. The bone mixture has 1.5 cc of mineralized cancellous bone 104, 1.5 cc of mineralized cortical bone 105 and 2.0 cc of demineralized cortical bone 106 yielding 30 percent, 30 percent and 40 percent respectively of the total 5 cc (5 gram) of bone material 102. The ranges coincide with the 1 cc of mixture when resuspended in 3 cc of saline to provide a bone and mixture for implantation, which can be by packing, injection, scaffolding or any other suitable means, into a patient in a fracture healing procedure, by way of example.

The bone mixture may be cortical or cancellous or any combination of both. The bone can be mineralized or demineralized or any combination of both. The bone may be in any form or size or shape suitable for bone repair. Lower volumes and cell counts may be more suited for less intrusive bone repairs or more if larger if larger amounts of material are needed as in a hip defect or repair.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of preparing a biological composition for implantation into a patient, the method of preparing the biological composition comprises the steps of:
    collecting, recovering and processing cadaverous bone including cortical bone, cancellous bone, and bone marrow cut from vertebral bodies from a cadaver donor;
    mechanically separating cellular and non-cellular components of bone marrow from cadaverous bone by tumbling, sieving the cadaverous bone from a decanted fluid of the bone marrow containing the cellular and non-cellular components in a series of cycles, wherein in a first cycle, the decanted fluid is discarded, and in subsequent cycles, the decanted fluid is collected and commingled to form the decanted fluid;
    concentrating the decanted fluid by centrifugation and filtering the decanted fluid through a blood filter to form a mixture including the cellular and non-cellular components separated from the marrow tissue and remaining cancellous and cortical bone that is discarded;
    separating the mixture by density gradient centrifugation to form an interface of the cellular and non-cellular components;
    collecting from the interface cells or non-cellular components or combinations thereof;
    washing the cells or non-cellular components or combinations thereof in the mixture;
    quantifying a cell concentration in the mixture, the cell concentration can be zero or greater;
    suspending the mixture in a cryoprotectant to create the biological composition for implantation, the biological composition being configured to be directly implanted without washing or rinsing;
    freezing the composition; and
    packaging a volume of bone separate from the composition to be added upon thawing or within the composition prior to freezing the mixture and cryoprotectant.

2. The method of preparing the biological composition use of claim 1 by the steps of:
    thawing the composition; and
    implanting the composition with or without the bone being intermixed with the mixture and cryoprotectant by packing, injection or any other suitable means into a patient.

3. The method of preparing the biological composition of claim 2 wherein the step of thawing the composition comprises the step of placing the composition in a water bath for 2 to 3 minutes wherein the water bath has a temperature of 37 degrees C.

4. The method of preparing the biological composition of claim 2 further comprises the step of:
    diluting the thawed composition in saline without spinning.

5. The method of preparing the biological composition of claim 3 further comprises the step of:
    diluting the thawed composition in saline without spinning.

* * * * *